US00PP19576P2

(12) United States Plant Patent
Bradford

(10) Patent No.: US PP19,576 P2
(45) Date of Patent: Dec. 16, 2008

(54) INTERSPECIFIC TREE NAMED 'BLACKRED V'

(50) Latin Name: *Prunus*
Varietal Denomination: Blackref V

(76) Inventor: Lowell Glen Bradford, 10237 E. Mariposa Way, Le Grand, CA (US) 95333

( * ) Notice: Subject to any disclaimer, the term of this patent is extended or adjusted under 35 U.S.C. 154(b) by 0 days.

(21) Appl. No.: 11/984,899

(22) Filed: Nov. 26, 2007

(51) Int. Cl.
*A01H 5/00* (2006.01)

(52) U.S. Cl. ..... Plt./180
(58) Field of Classification Search ..... Plt./180
See application file for complete search history.

(56) References Cited

U.S. PATENT DOCUMENTS

PP14,196 P2 9/2003 Bradford
PP14,219 P2 10/2003 Bradford

*Primary Examiner*—Annette H Para
*Assistant Examiner*—S. B. McCormick-Ewoldt

(57) ABSTRACT

The present invention relates to an interspecific tree and more particularly to a medium size, vigorous, hardy, and productive tree. The present variety has a prolific bloom during the early to mid season, is self-unfruitful, but produces an abundance of pollen to entice bees to facilitate pollination. The fruit matures under the ecological conditions described during early July, with first picking on Jun. 30, 2007. The fruit is uniformly medium in size, blackish red in skin color, clingstone in type, globose to obovate in shape, dark red in flesh color, firm and crisp in texture, and outstanding in flavor.

1 Drawing Sheet

Botanical classification: *Prunus* sp.
Varietal denomination: 'Blackred V'.

BACKGROUND OF THE VARIETY

In a continuing effort to improve the quality of shipping fruits, I, the inventor, typically hybridize a large number of peach, nectarine, plum, apricot, and cherry seedlings each year. I also grow a lesser number of open pollinated seeds of each of these fruits. The present invention relates to a new and distinct variety of interspecific tree, which has been denominated varietally as 'Blackred V'.

During a typical blooming season I isolate as seed parents both individual and groups of different plum trees by covering them with screen houses. A hive of bees is placed inside each such house, and bouquets to provide pollen from different plum, apricot, and interspecific plum-apricot hybrid trees are placed in buckets near the trees approximately every two days for the duration of the bloom. During 2001 one such house containing an unpatented red plum, code named 19P442, was crossed by me in this manner. To pollinate this red plum, I selected bouquets from several sources of apricot and interspecific plum-apricot hybrid trees without keeping specific written details. Upon reaching maturity the fruit from this red plum tree was harvested and the seeds were removed, cracked, stratified and germinated as a group with the label "HBA". They were grown as seedlings on their own root in my greenhouse and upon reaching dormancy transplanted to a cultivated area of my experimental orchard located near Le Grand, Calif. in Merced County (San Joaquin Valley). During the summer of 2004 the claimed variety was selected by me as a single plant from the group of seedlings described above. Subsequent to origination of the present variety of interspecific tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is similar to 'Plumsweettwo' (U.S. Plant Pat. No. 14,196) plum by being self-unfruitful and by producing fruit that is medium in size, that is clingstone in type, that is nearly black in skin color, and that is dark red in flesh color, but is distinguished therefrom by having a more prolific bloom, by producing much more pollen, and by producing fruit that has a less distinguishable suture, that has less pronounced freckling, and that matures about twenty-five days earlier.

SUMMARY OF VARIETY

The present interspecific variety is characterized by a medium size, vigorous, hardy, and productive tree. Being self-unfruitful, the present variety requires cross pollination from an apricot, interspecific, or plum that blooms during the early to mid season. The present variety's abundance of blossoms and pollen entices strong bee activity to facilitate pollination. The fruit matures under the ecological conditions described during early July, with first picking on Jun. 30, 2007. The fruit is uniformly medium in size, blackish red in skin color, clingstone in type, globose to obovate in shape, dark red in flesh color, firm and crisp in texture, and outstanding in flavor.

DRAWING

The accompanying photograph consists of four whole fruits positioned to display the characteristics of the skin color and form, one half of a fruit divided transversely to the suture plane to reveal the flesh and stone, a freshly cleaned stone, a young tip shoot growth, typical leaves, and two insets depicting the flower buds and blossoms as they appeared on the tree during the blooming season.

DETAILED BOTANICAL DESCRIPTION

Referring now more specifically to the pomological characteristics of this new and distinct variety of interspecific tree, the following has been observed under the ecological conditions prevailing near Le Grand, Merced County (San Joaquin Valley), Calif. The fruit description was developed at the state of full ripe on Jul. 10, 2007, on the original tree during its sixth growing season. The flower and bud descriptions were developed during the previous blooming season. All major color code designations are by reference to the Inter-Society Color Council, National Bureau of Standards. Common color names are also used occasionally.

Parentage

Seed parent: 19P442 plum (unpatented).
Pollen parent: Unknown.

Tree

Size: Medium, reaching and maintaining a height of 12' [3.66m.]and a spread of 7' [2.13 m.] after six growing seasons utilizing typical dormant pruning.

Vigor: Vigorous, responding typically to irrigation and fertilization. The variety grows about 4' [1.22 m.] of surplus top-growth during the spring and summer. The plant should be grown on a standard commercial rootstock for production purposes.

Growth: Upright and dense.

Form: Pruned to a vase form.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Very productive, thinning usually necessary.

Fertility: Self-unfruitful, requiring cross pollination by a suitable mid seasonal blooming apricot, interspecific, or plum, such as 'Plumsweetone' U.S. Plant Pat. No. 14,219).

Bearing: Regular bearer, with no crop failures observed.

Trunk:

*Size.*—Medium, reaching a maximum diameter of 3" [76.2 mm.] after the sixth growing season.

*Texture.*—Shaggy.

*Bark color.*—A Dark grayish brown [62. d.gy.Br.] and Deep yellowish brown [75. deep yBr] variegation with Strong yellowish brown [74. s.yBr] crevices present.

*Lenticels.*—Approximate Number Per Square Inch: 4. Color: Strong yellowish brown [74. s.yBr]. Average Size: ¼" [6.4 mm.]. Shape: Eye-shaped, elongated.

Branches:

*Size.*—Diameter of limb is 2" [50.8 mm.] measured 12" above the crotch, 1¼" [31.8 mm.] measured 12" above the first fork.

*Texture.*—Smooth on first and second year wood, increasing roughness with age.

*Color.*—1st Year Wood Topside: Light reddish brown [42. l.rBr]. 1st Year Wood Underside: Brilliant yellow green [116. brill.YG]. Older Wood: Brownish gray [64. brGy].

*Lenticels.*—Number Per Square Inch: More than 80 on second year wood. Color: Light yellowish brown [76. l.yBr]. Average Size: 1/32" [0.8 mm.]. Shape: Rectangular, elongated.

Leaves:

*Size.*—Large. Average Length: 4 1/16" [103 mm.]. Average Width: 1⅞" [48 mm.].

*Arrangement.*—Alternate.

*Thickness.*—Medium.

*Form.*—Elliptical.

*Apex.*—Acuminate to mucronate.

*Base.*—Acute with an average angle base angle of 80 degrees.

*Surface.*—Smooth.

*Color.*—Dorsal Surface: Moderate olive green [125. m.OlG]. Ventral Surface: Moderate yellow green [120. m.YG].

*Margin.*—Finely serrate.

*Venation.*—Pinnately net veined.

*Petiole.*—Average Length: 5/16" [7.9 mm.]. Average Thickness: 1/16" [1.6 mm.]. Color: Strong yellow green [117. s.YG] underneath, Dark red [16. d.R] in the sunlight.

*Stipules.*—Number: 2 per leaf, up to 6 per growing tip. Average Length: ¼" [6.4 mm.]. Color: Very yellow green [115. v.YG] becoming Moderate reddish brown [43. m.rBr] with age.

*Glands.*—Number: 6 to 12 per leaf. Position: Oppositely positioned on the petiole in a unique pair of tightly packed rows. Size: Very small. Form: Globose. Color: Brilliant yellow green [116. brill.YG] becoming Moderate red [15. m.R] in the center with age. Leaf buds: Pointed, medium.

Flower buds:

*Hardiness.*—Hardy, with respect to central California winters.

*Diameter.*—Typically 3/16" [4.8 mm.] 1 week before bloom.

*Length.*—Typically ⅜" [9.5 mm.] 1 week before bloom.

*Form.*—Not appressed.

*Surface.*—Pubescent.

*Tip color.*—White [263. White].

Flowers: Perfect, complete, perigynous, usually a single pistil, typically thirty or more stamens, five sepals and petal locations alternately positioned.

*Average flower diameter.*—1" [25.4 mm.].

*Number of petals.*—Five, no double blossoms observed.

*Petal shape.*—Oval to circular.

*Petal margin.*—Entire, somewhat wavy with notches typical.

*Average petal diameter.*—½" [12.7 mm.].

*Average petal length.*—9/16" [14.3 mm.].

*Petal apex.*—Rounded.

*Petal Base.*—Obtuse.

*Petal Color.*—White [263. White] on both sides.

*Anther color.*—Deep orange yellow [69. deep OY].

*Stigma color.*—Brilliant greenish yellow [98. brill.gY].

*Sepal color.*—Brilliant yellow green [116. brill.YG].

*Sepal length.*—3/16" [4.8 mm.].

*Sepal width.*—5/32" [4.0 mm.].

*Sepal Apex.*—Rounded to elliptical to match the width and length.

*Sepal margin.*—Fairly smooth to the naked eye, slightly serrate when magnified.

*Average pistil length.*—3/8" [9.5 mm.], shorter than normal.
*Average stamen length.*—1/2" [12.7 mm.].
*Fragrance.*—Strong.
*Pollen production.*—Abundant, very bee enticing.
*Blooming Period..*—Somewhat early, two days after 'Ambra' plum (unpatented).
*Onset of bloom.*—One percent on Feb. 24, 2007.
*Date of full bloom.*—Mar. 4, 2007.
*Duration of bloom.*—One to two weeks, dependent on ambient temperature.
*Bloom density.*—Exceedingly heavy.
*Number per cluster.*—2 to 12, average 7.

FRUIT

Maturity when described: Firm ripe, Jul. 10, 2007.
Date of first picking: Jun. 30, 2007.
Date of last picking: Jul. 10, 2007.
Size: Uniform, Medium.
*Average diameter axially.*—2 1/16" [52.4 mm.].
*Average diameter across cheek plane.*—2 3/8" [60.3 mm.].
*Average diameter across suture plane.*—2 7/16" [61.9 mm.].
*Typical weight.*—4.3 ounces [122 grams].
Form: Uniform, Globose to somewhat obovate, symmetrical.
*Longitudinal section form.*—Round to somewhat obovate.
*Transverse section through diameter.*—Round.
Suture: An inconspicuous line located in a very shallow groove extending from the base to the apex.
Ventral Surface: Rounded, lipped very slightly toward the base.
Lips: Equal.
Cavity: Flaring, rounded, suture showing on one side.
*Depth.*—5/16" [7.9 mm.].
*Breadth.*—7/8" [22.2 mm.].
Base: Truncate, somewhat cordate if viewed parallel to the suture.
Apex: Rounded with a small hump at the pistil point.
Pistil Point: An inconspicuous dot.
Stem: Medium.
*Average length.*—3/8" [9.5 mm.].
*Average Width.*—5/64" [2.0 mm.].
Skin:
*Thickness.*—Medium.
*Surface.*—Smooth.
*Tenacity.*—Tenacious to the flesh.
*Astringency.*—Slight.
*Tendency to crack.*—Almost none.
*Color.*—Blackish red [21. blackish R] with very small Pale orange yellow [73. p.OY] freckling throughout.
*Bloom.*—Abundant.
Flesh:
*Color.*—Very deep red [14. v.deep R] toward the skin, Dark red [16. d.R] toward the stone.
*Surface of pit cavity.*—Covered with Very dark red [17. v.d.R] broken fibers when twisted from the stone.
*Amygdalin.*—Moderate.
*Juice.*—Abundant, rich.
*Texture.*—Firm, crisp.
*Fibers.*—Abundant, fine, tender.
*Ripens.*—Slightly earlier toward the apex.
*Flavor.*—A tasty blend of acid and sugar, typically 22 brix.
*Aroma.*—Moderate.
*Eating quality.*—Outstanding.

STONE

Type: Clingstone.
Form: Oval.
Hilum: Narrow.
Base: Straight.
Apex: Mucronate, with a sharp 3/32" [2.4 mm.] tip.
Sides: Equal.
Surface: Rough throughout with a groove on each side of the dorsal fin.
External color of stone: Strong yellowish brown [74. s.yBr].
Pit wall color when cracked: Light grayish yellowish brown [79. l.gy.yBr].
Cavity surface color: Light yellowish brown [76. l.yBr].
Average pit wall thickness: 1/16" [1.6 mm.].
Average width: 11/16" [17.5 mm.].
Average length: 1" [25.4 mm.].
Average breadth: 7/16" [11.1 mm.].
Tendency to split: None observed.
Kernel:
*Form.*—Oval.
*Skin color.*—Pale yellow [89. p.Y] when first removed.
*Pellicle color.*—Deep yellowish brown [75. deep yBr].
*Vein color.*—Light yellowish brown [76. l.yBr].
*Taste.*—Bitter.
*Viable.*—Yes.
*Average Width.*—3/8" [9.5 mm.].
*Average length.*—1/2" [12.7 mm.].
*Amygdalin.*—Abundant.

Use

Market: Fresh market and long distance shipping.
Keeping quality: Good, fruit quality observed to remain in good condition after 21 days in standard cold room at 36° Fahrenheit [2° Celsius].
Shipping quality: Good.
Resistance to insects: No unusual susceptibilities noted.
Resistance to diseases: No unusual susceptibilities noted.

Other Notes

Although the new variety of interspecific tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of interspecific *Prunus* sp. tree, substantially as illustrated and described, that is similar to 'Plumsweettwo' U.S. Pat. No. 14,196) plum by being self-unfruitful and by producing fruit that is medium in size, that is clingstone in type, that is nearly black in skin color, and that is dark red in flesh color, but is distinguished therefrom by having a more prolific bloom, by producing much more pollen, and by producing fruit that has a less distinguishable suture, that has less pronounced freckling, and that matures about twenty-five days earlier.

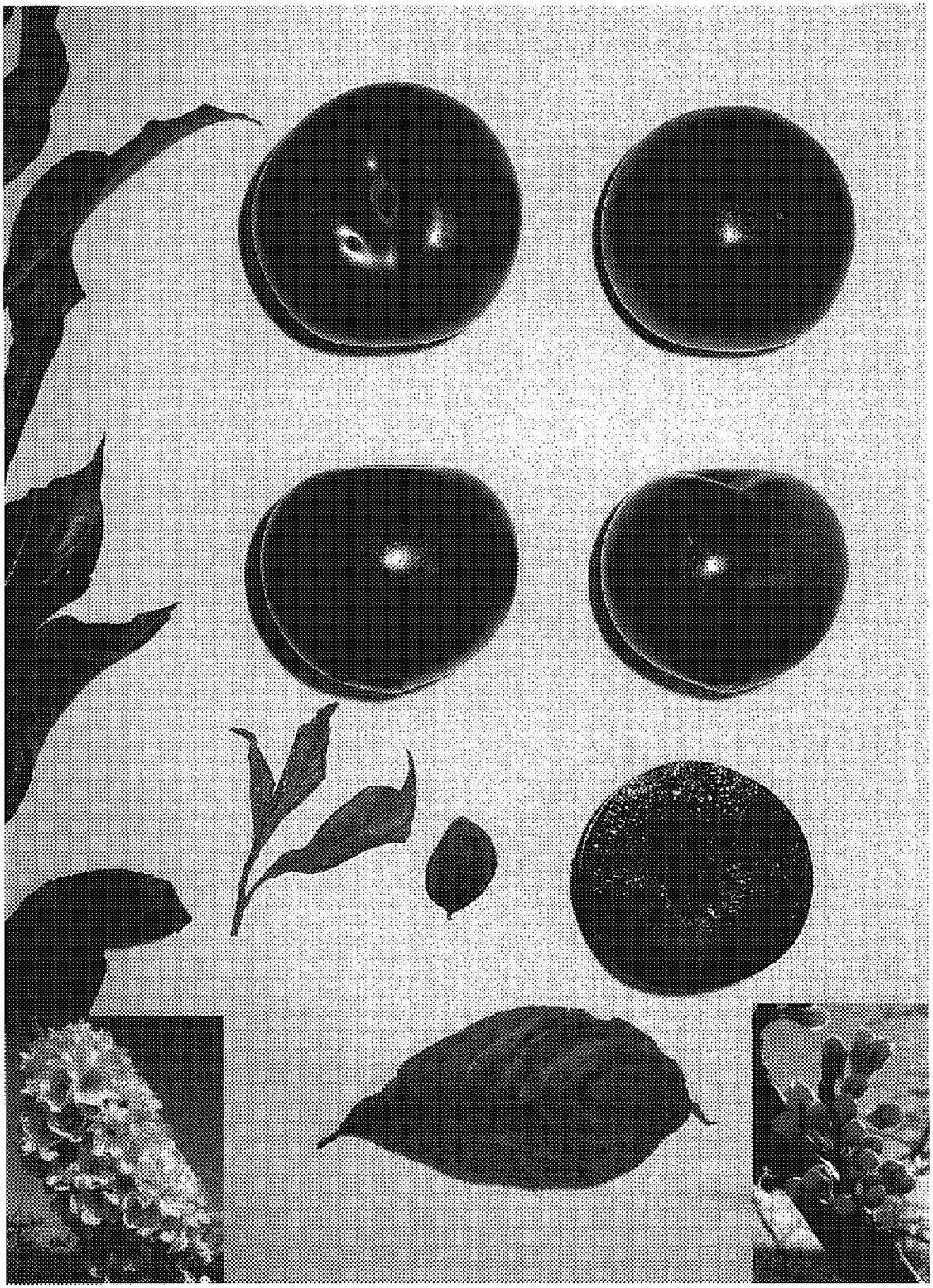

* * * * *